United States Patent
Heenan et al.

(10) Patent No.: US 9,651,974 B2
(45) Date of Patent: May 16, 2017

(54) ELECTRICAL POWER TRANSMISSION LINE LENGTH MEASUREMENT AND AVERAGE TEMPERATURE ESTIMATION

(71) Applicant: Southwest Research Institute, San Antonio, TX (US)

(72) Inventors: Patrick R. Heenan, Boulder, CO (US); Ben A. Abbott, San Antonio, TX (US); Gary L. Ragsdale, San Antonio, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 455 days.

(21) Appl. No.: 14/529,031

(22) Filed: Oct. 30, 2014

(65) Prior Publication Data

US 2016/0124449 A1 May 5, 2016

(51) Int. Cl.
| | |
|---|---|
| *H02J 3/00* | (2006.01) |
| *G05F 1/66* | (2006.01) |
| *G01N 27/00* | (2006.01) |
| *G01B 7/02* | (2006.01) |
| *G01K 3/06* | (2006.01) |
| *G01B 7/16* | (2006.01) |

(52) U.S. Cl.
CPC ............... *G05F 1/66* (2013.01); *G01B 7/026* (2013.01); *G01K 3/06* (2013.01); *G01N 27/00* (2013.01); *H02J 3/00* (2013.01); *G01B 7/16* (2013.01)

(58) Field of Classification Search
CPC .................................. G01N 27/00; H02J 3/00
See application file for complete search history.

(56) References Cited

PUBLICATIONS

Slegers, James. "Transmission Line Loading Sag Calculations and High-Temperature Conductor Technologies", Iowa State University, Oct. 18, 2011.

*Primary Examiner* — Adi Amrany
(74) *Attorney, Agent, or Firm* — Livingston Law Firm

(57) ABSTRACT

A system and method for measuring length of an electrical power transmission line, and for estimating the average temperature of the line over the measured length. A signal is applied to the line and reflected from a reflection point to obtain a present measure of the line's length. A modified catenary equation uses the length measurement and other variables to estimate average temperature. This temperature measurement can then be used to determine how much power the line is presently capable of safely carrying.

7 Claims, 5 Drawing Sheets

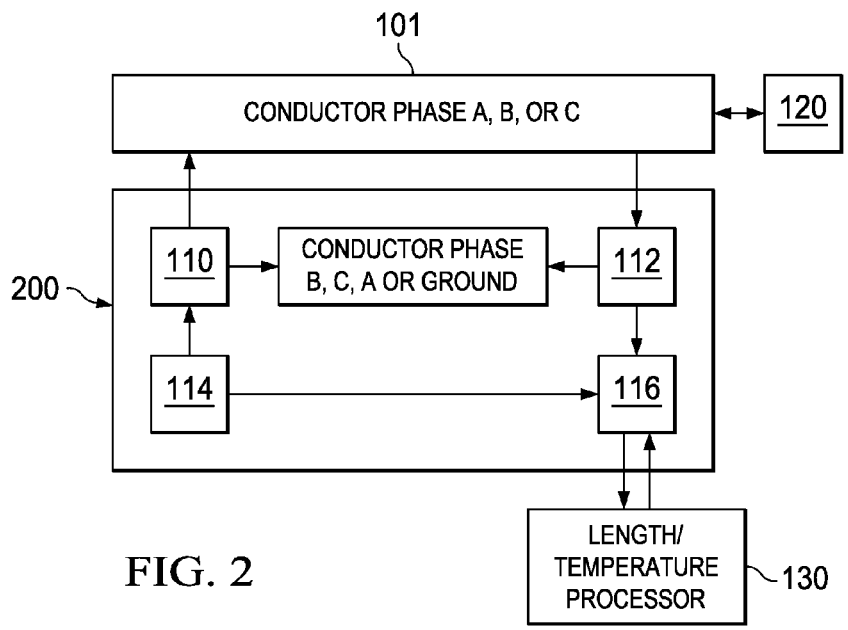

FIG. 2

| WAVEFORM NAME | FREQUENCY CONTENT IN BIN $t_x$ | | | | | DESCRIPTION OF SIGNAL OVER TIME |
|---|---|---|---|---|---|---|
| | $t_0$ | $t_1$ | ○ ○ ○ | $t_{n-1}$ | $t_n$ | |
| FREQUENCY HOP | $f_0$ | $f_1$ | ○ ○ ○ | $f_{n-1}$ | $f_0$ | SINGLE-CHANNEL, DISCRETIZED FREQUENCY MODULATION |
| SPREAD SPECTRUM FREQUENCY HOP | $\sum_{k_0}^{k_{N0}} f_{k_0}$ | $\sum_{k_1}^{k_{N1}} f_{k_1}$ | ○ ○ ○ | $\sum_{k_{(n-1)}}^{k_{N(n-1)}} f_{k(n-1)}$ | $\sum_{k_0}^{k_{N0}} f_{k_0}$ | MULTIPLE-CHANNEL, DISCRETIZED FREQUENCY MODULATION |
| SPREAD SPECTRUM FREQUENCY MODULATION | $\sum_{k}^{N} f_k(t_x)$ | | | | | MULTIPLE-CHANNEL, CONTINUOUS FREQUENCY MODULATION |

FIG. 3

$$V_{in,k}(t) = \sum_{k=0}^{N_{in}-1} \tilde{a}_k e^{i\omega_k t} \qquad V_{out,j}(t) = \sum_{j=0}^{N_{out}-1} \tilde{b}_j(t) e^{i\omega_j t}$$

$$\tilde{H}(\omega_k) = \frac{V_{out,j=k}(t)}{V_{in,k=k}(t)} = \frac{\boxed{\tilde{b}_k(t)}}{a_k} = \frac{\boxed{\tilde{n}_k(t)} + \boxed{\tilde{b}_k(t)}}{a_k}$$

FREQUENCY RESPONSE (pointing to $\tilde{b}_k(t)$)

NOISE COEFFICEINT (pointing to $\tilde{n}_k(t)$)

REFLECTION CONSTANT (pointing to $\tilde{b}_k(t)$)

WHERE, $\tilde{b}_k = \tilde{a}_k e^{i\omega_k(\theta_k + t_\varphi)} |r_k|$

FIG. 6

$$T_k = (\theta_k + t_\varphi) = \frac{1}{\omega_k} \tan\left(\frac{\text{Im}(\tilde{H}(\omega_k))}{\text{Re}(\tilde{H}(\omega_k))}\right)$$

FIG. 7

| METHOD FOR REDUCING $T_k = (\theta_k + t_\varphi)$ | ASSUMPTIONS |
|---|---|
| CORRECT $T_{k>0}$ BY SOLVING $(\theta_{j>0} - \theta_k)$ FOR ALL BANDS | $\theta_0$ IS KNOWN OR SMALL COMPARED TO $(\theta_0 - \theta_{m!=0})$. $T_k$ IS DIFFERENTIABLE FOR ALL k |
| DETERMINE $t_\varphi$ BY MINIMIZING $\dfrac{\tilde{H}(\omega_l)}{\|\tilde{H}(\omega_l)\|} e^{-i\omega_l \tau z}$ FOR $0 < \tau < (\theta_k + t_\varphi)$ | $t_\varphi \gg \theta_k$ |
| DETERMINE $\theta_k$ BY MINIMIZING $\dfrac{\tilde{H}(\omega_l)}{\|\tilde{H}(\omega_l)\|} e^{-i\omega_l \tau z}$ FOR $0 < \tau < (\theta_k + t_\varphi)$ | $\theta_k \gg t_\varphi$ |

FIG. 8

$$L = L_0 \times (1 + \alpha_T \times \{T - T_0\}) \left\{ 1 + \frac{H - H_0}{E_0 \times A} + \varepsilon_C \right\}$$

$$T = \frac{2H_0(\alpha_T T_0 - 1) \times (H - H_0 + AE_0 \times \{1 + \varepsilon_C\}) + AE_0 L_w \times \operatorname{csch}\left[\frac{l_w}{2H_0}\right]}{2H_0 \alpha_T \times \{H_0 - H - AE_0(1 + \varepsilon_C)\}}$$

ELECTRICAL POWER TRANSMISSION LINE LENGTH MEASUREMENT AND AVERAGE TEMPERATURE ESTIMATION

TECHNICAL FIELD OF THE INVENTION

This invention relates to overhead electrical power transmission lines, and more particularly to estimating their average temperature from length measurements.

BACKGROUND OF THE INVENTION

The "electric grid" can be described in terms of its most basic elements as a collection of generation, transmission, and distribution systems. Transmission utilities transport energy from generators to end-user distribution systems over high-voltage transmission lines. Power is dispatched from the generators and distributed among transmission lines based in part on capacity ratings of the transmission line.

The transmission line (also referred to herein as "the conductor" or "the line") has an ampere carrying capacity ("ampacity") rating that is constrained by two limits: (1) the conductor's position relative to the tower attachment points ("sag") and (2) the maximum design temperature of the conductor material.

The amount of sag is directly related to the amount of current the conductor carries and hence to its temperature; if there is too much current and too high of a temperature, there is a risk of too much sag. Utilities must limit the amount of sag to prevent arcing from the conductor to objects or the ground. If the maximum conductor design temperature is exceeded permanent deformation of the conductor (e.g., inelastic elongation or expansion) occurs.

In addition to the amount of current the conductor is carrying, the temperature of a transmission line is also greatly affected by wind against the line. This of course, can vary greatly along the route of the line, making it difficult to discern the actual temperature variation along the line. Conventionally, to stay within temperature constraints, it is not expected to know the actual temperature distribution along the transmission line. The maximum current load is set as a compromise between an estimation of temperature conditions and risk minimization.

More recently, attempts have been made to provide real time temperature monitoring along the transmission line. Various types of sensors have been used to directly measure temperature on the transmission line. The object of temperature monitoring is to better achieve power distribution according to the actual capacity of the transmission line.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein:

FIG. 2 illustrates the signal generator/detector of FIG. 1 in further detail.

FIG. 3 illustrates candidate waveforms, increasing in number of channels and bandwidth.

FIG. 6 illustrates a transfer function used in computing the time delay of the reflected signal.

FIG. 7 illustrates how the total delay time is calculated for each frequency band.

FIG. 8 illustrates various methods for isolating the time difference of interest from the total delay time.

DETAILED DESCRIPTION OF THE INVENTION

Figure 1:
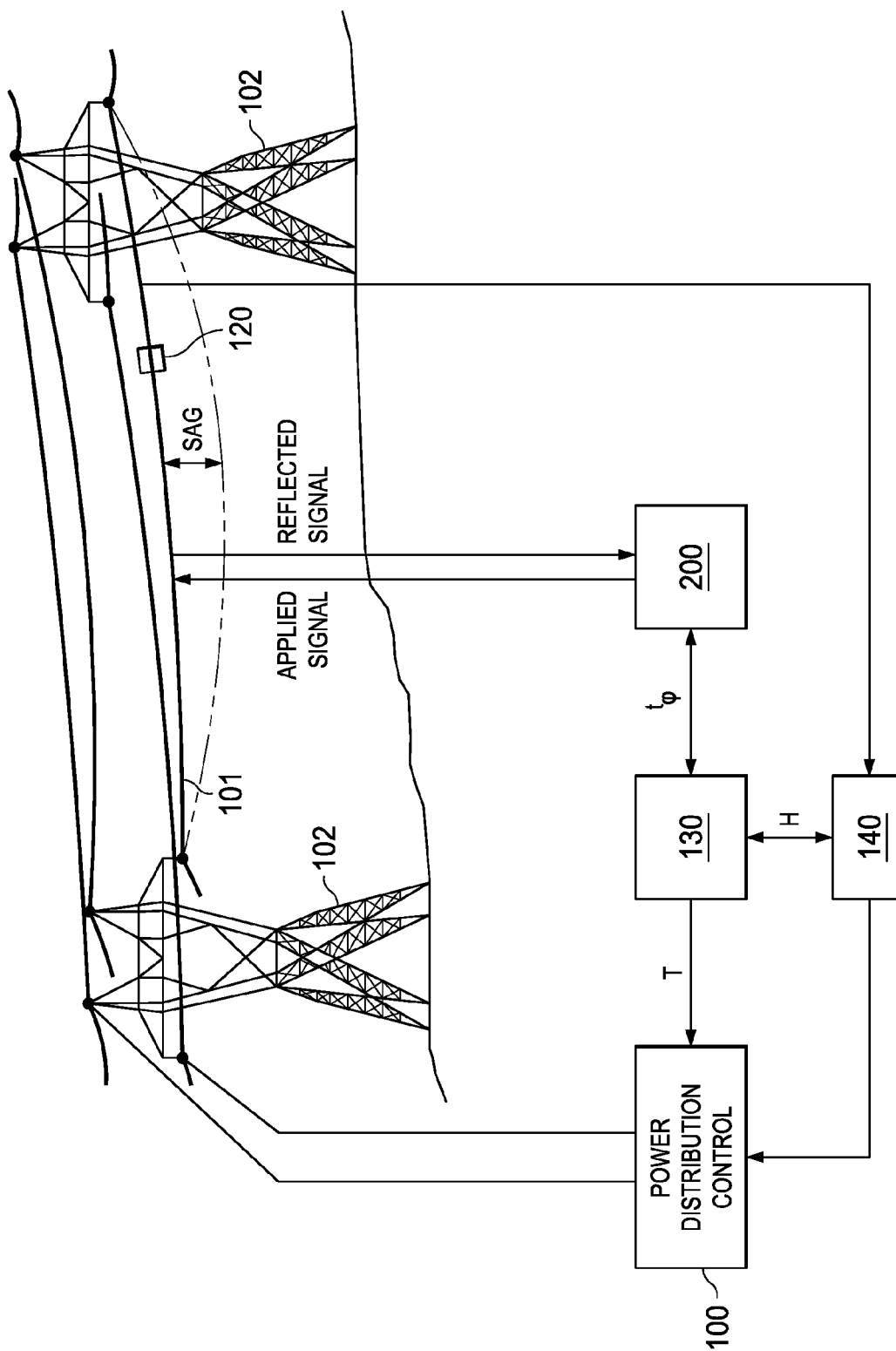
FIG. 1 illustrates a transmission line and a system for measuring its length and estimating its temperature from the length measurement, and for distributing power to the line based on those measurements.

The following description is directed to a system and method for measuring the length of overhead electrical power transmission lines. For purposes of simplicity, these transmission lines are also referred to herein as "conductors" or "lines".

As explained below, the length measurements are based on the transit time of a signal to travel from its source to a reflector and back to the source. More specifically, a signal waveform of known characteristics is sent over the conductor, and is reflected at a reflection point along the conductor. The reflection signal is detected, and the reflection propagation delay is measured to accuracies of up to 9.8 ($10^{-12}$) seconds.

As indicated in the Background, a transmission line's temperature will increase as it carries more current, resulting in sag. In other words, the length of the transmission line varies with its temperature. As an example, a 604 foot length of a typical transmission line may vary in length by six inches over its full range of operating temperatures, Typical operating temperatures range from 25 degrees C. to 75 degrees C.

It is well understood in the field of transmission line analysis that the temperature of the transmission line at any one point is not a good indicator of the temperature at other points. This is because the conductor temperature is highly affected by both the amperage carried by the conductor and the orthogonal velocity of the wind on the conductor.

Based on measurements of transmission line length, the system and method further calculate the real-time average temperature of the conductor. No temperature sensors are required to be placed on the line, and the method provides an average temperature over the measured length of the line, as opposed to point measurements.

As used herein, the "average conductor temperature" is an average of temperatures over the measured length of the transmission line. This average temperature data is further used to determine how much current-carrying capacity the conductor presently has. To eliminate confusion with electrical "current", the real-time measured length and estimated average temperature values are referred to herein as "present" values.

A typical transmission line is a time-variant complex-impedance communications channel with high-energy waveforms at low frequency, synchronous and asynchronous impulse noise, white noise, and radio frequency (RF) interference imposed on the communications channel from 0 to 100 MHz. Reflective mechanical couplings, switch closures, and mismatched impedances add time-varying, multipath reflections to an already impaired channel.

The method achieves measurement of conductor length in the noisy, impaired environment typical of an electric transmission line. It accurately obtains the conductor length despite the limitations imposed by the environment and signal coupling, required frequency of temperature estimation, and realistic conductor non-linearity. The method achieves improved length accuracy through greater propagation delay precision, using advanced signal correlation techniques, phase difference comparators, and dual signal mixer delay counters.

FIG. 1 illustrates a transmission line 101 and a system for measuring its length and estimating its temperature from the length measurement, and for distributing power to the transmission line based on those measurements. In this example, transmission line 101 is one of three lines suspended between two towers 102. The flexible transmission line 101 supported at its ends approximates the form of a catenary curve.

Transmission line 101 is assumed to be of the kind common to electric power transmission and feeder lines, such as high voltage, "Drake" aluminum core, and/or steel reinforced (ACSR) transmission line conductors. It is insulated from ground using floating insulators, dielectric materials, or other means sufficient to maintain electrical isolation.

As indicated by the dotted line, the transmission line 101 has a "sag" value, which is the vertical distance between the highest and lowest points of the conductor's curve. As stated above, sag varies depending on the temperature of the conductor, which increases with increasing heat produced by the current through it.

Reflection point 120 reflects an applied signal to produce a reflected signal. As explained below, for length measurements, reflection point 120 may be a reflection device placed on the conductor 101 at a known position on the line. In general, for measuring length and average conductor temperature in the manner discussed below, reflection point 120 may be one of various electronic reflector devices placed on the conductor 101 that receives and sends back an applied signal. Ideally, a reflector for this purpose is suitable for permanent installation on conductor 101 to allow real time measurements to be obtained at any desired time.

For other applications such as fault detection, reflection point 120 may also be an as-built reflection point or an incidental high-impedance reflection point. A feature of the invention is that more than one reflection point may be detected, and the reflection points differentiated.

The system for measuring conductor length, estimating average conductor temperature, and determining line capacity is illustrated as a high level illustration. Each of these elements are described in further detail herein, but as an overview, signal generator/detector 200 delivers an applied signal to conductor 101 and receives a reflected signal. A length/temperature processor 130 calculates the time difference of the applied and reflected signals, and from that data, calculates real-time conductor length and average conductor temperature. Sag/tension measurement unit 140 may be a commercially available device that measures conductor tension and sag. Power distribution controller 100 uses the data provided by processor 130 and line rating unit 140 to determine how much power is to be transmitted on line 101 at any given time.

FIG. 2 illustrates signal generator/detector 200 in further detail. Signal injection coupler 110 is electrically connected to conductor 101, and is operable to inject complex signals onto conductor 101. Signal injection coupler 110 provides electrical isolation between a complex waveform generator 114 and the conductor 101 for signal frequencies below 10 KHz. It provides a radio frequency signal injection interface to conductor 101 for frequencies from 10 KHz and 100 MHz.

Signal reflection coupler 112 is electrically connected to conductor 101, and is operable to receive complex reflected signals. Signal reflection coupler 112 provides a radio frequency signal reception interface from conductor 101 to the complex waveform receiver 116 for frequencies between 10 KHz and 100. It provides electrical isolation between the complex waveform receiver and conductor 101 for signal frequencies below 10 KHz.

Waveform generator 114 generates and transmits waveforms of a prescribed configuration to signal coupler 110. A priori knowledge of the frequency content of the waveform allows for correlation with reflected signals and measurement of reflection length.

FIG. 3 illustrates candidate waveforms, increasing in number of channels and bandwidth. The frequencies used increase linearly in the region between 100 KHz and 10 MHz in steps on the order of 500 Hz. Each waveform has a fundamental period, $t_n$, after which it repeats itself. Although each waveform is theoretically applicable to conductors of any length, in practice, power consumption of a high-energy reference waveform and attenuation may limit the maximum conductor length.

Referring again to FIG. 2, waveform receiver 116 receives the applied signals produced by waveform generator 114 and the reflected signals produced by reflection point 120. Receiver 116 records and time stamps these signals and delivers them to processor 130.

Figure 4:
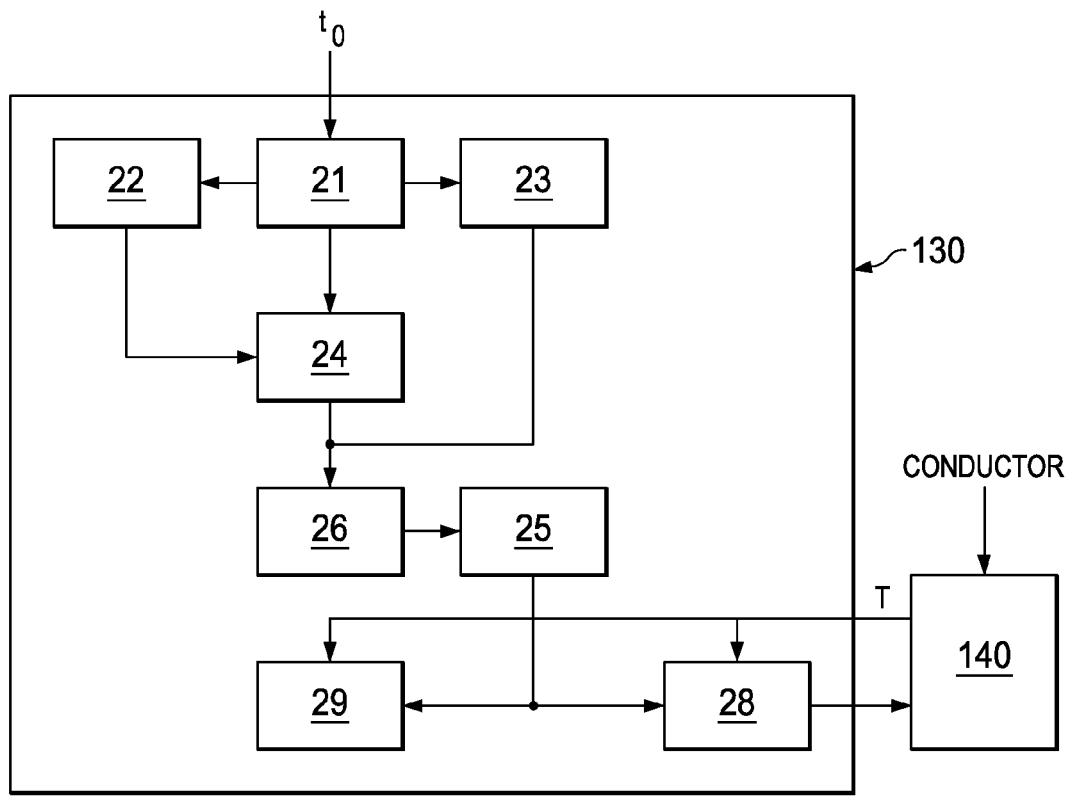
FIG. 4 illustrates the various processes performed by the length/temperature process of FIG. 1.

FIG. 4 illustrates the various processes performed by the length/temperature process 130 of FIG. 1. It is assumed that process 130 has appropriate hardware and software for performing the processing tasks described herein.

Waveform detection process 21 receives signals from waveform recorder 116, and converts these signals to data representing the injected and reflected signals. Detection process 21 separates signals recorded by receiver 116 by means of filters and frequency response compensation. The detected signals are made available to length calibration process 22, frequency response calibration process 23, and time difference process 24.

One or more matched filters may be used to detect the reflected waveforms. The waveform detection process 21 uses waveform information supplied by waveform generator 116 to down-select the matched filter candidates to those most likely to detect the waveform reflection. The types of matched filters used by the waveform detection process 21 include, but are not limited to, post-processing band-pass filters, using a priori knowledge of the input frequency bands from waveform generator 116.

The matched filter of process 21 detects the waveform and produces a propagation delay estimate using correlation or similar behavior comparison techniques. The waveform detection process 21 adaptively compensates for signal impairments caused by conductor reactance using the methods discussed below in connection with the time difference process 24.

A conductor length calibration process 22 derives the conductor length to reflection point 120, which is placed on the conductor 101 at a known distance from the signal injection point and at a known conductor temperature. The calibrated conductor length and temperature values are used as inputs to the conductor length process 26.

A frequency response calibration process 23 receives signal data from process 21 and derives the conductor's frequency response to injected signals across an operational frequency range. The frequency response is then used to optimize the operation of signal generator 116 and conductor length process 26.

Figure 5:
FIG. 5 illustrates mathematical expressions for the input signal and the reflection signal, respectively.

FIG. 5 illustrates mathematical expressions for the input signal and the reflection signal, respectively. The input signal is real-valued with known frequency content. The reflection signal contains time variant noise and reflections. There is no assumption that $N_{out}=N_{in}$. In the following discussion, "tildes" are dropped if they are implicit.

As illustrated in FIG. 6, computing a transfer function allows for notching to the input "k" band. The frequency response is broken into a time-variant noise coefficient and a time-variant reflection constant. In the expression for frequency response, $|r_k|$ is the real valued attenuation of the medium, $\omega_k \theta_k$ is the phase shift in radians at the given frequency, and $t\phi$ is the propagation delay time of interest, which is assumed time and frequency invariant during each measurement.

FIG. 7 illustrates how, in a relatively low noise band, the total delay time can be measured for each band. The total phase shift due to electrical path length and time and frequency dependent channel characteristics can be given for each frequency $\omega_k$. This calculation compensates for frequency attenuation. $T_k$ is the total time difference, $\theta_k$ is the frequency-dependent phase response of the channel filter, and $t\phi$ is the time difference of interest. The delay, $t\phi$, can be isolated in the equation of $T_k$ by the method discussed below in connection with the time difference process 24.

The time difference process 24 calculates the propagation delay from the signal injection point to reflection point 120 and back. As stated above, the reflection point may be a reflector 120 placed on the conductor, an as-built reflection point, or an incidental high-impedance reflection point. The time difference values are transferred to processes 22, 23, 24, 25 and 26 for use within their respective processes.

FIG. 8 illustrates various methods for isolating the time difference of interest from the total time difference. Traditional methods for correlating a reference signal with a reflection, such as phase and power spectrum analysis, may also be used and compared to the methods illustrated in FIG. 8.

Referring again to FIG. 4, a conductor reflection profile process 25 distinguishes between reflection devices, as-built reflection points, and incidental high-impedance reflection points. It does so using a combination of system operator-supplied information, reflected signal characteristics compiled over time into a chronological database, and comparisons to newly detected reflected signals. Operator-supplied information may give a number of factors including the location of reflection devices, signal injection point locations, and known as-built reflection points. A chronological database of reflected signal characteristics is used to compute the position of persistent reflection points identifiable as as-built reflection points.

During length measurements, process 25 may use its stored data to differentiate between signals reflected from inherent features of the line (referred to generally as "faults") and the desired reflected signal, e.g., the signal reflected from an electrical reflector purposefully serving as a reflection point. For applications other than length and temperature measurement, process 25 may use the database to detect and evaluate recent appearances of reflected signals for the presence of new fault conditions on the conductor.

A conductor length method process 26 calculates the conductor length from the signal injection point to the reflection point 120. It does so using data supplied by process 24, as well as calibration information provided by process 22 to compute the conductor signal propagation velocity and conductor length.

As shown in both FIGS. 1 and 4, line rating unit 140 measures the present conductor tension and sag. Process 140 may be implemented with commercially available equipment. Various known measurement sensors may be used. For example, unit 140 may use a sensor such as a strain gauge to obtain a tension measurement. The tension measurements are used for the calculation of conductor temperature by process 28.

An average conductor temperature process 28 calculates the average conductor temperature, which is an estimate of an average of temperatures along the length of the conductor as measured by process 26. Thus, the average conductor temperature process 28 receives conductor length data from process 26. It also receives tension measurements from line rating unit 140. Additional data is operator supplied, such as conductor type, distance between adjoining towers, conductor unit weight, and other information. As stated above, process 22 supplies a calibrated length of the conductor at a known conductor temperature.

The average conductor temperature process 28 uses the supplied information and a catenary equation to estimate the average conductor temperature. The "catenary equation" is referred to as such because it is a modification of an equation representing a catenary curve of a span at constant temperature. The modifications of the catenary equation contains variables that affect the length of a conductor having temperature variations along its length.

Figures 9, 10, 11:
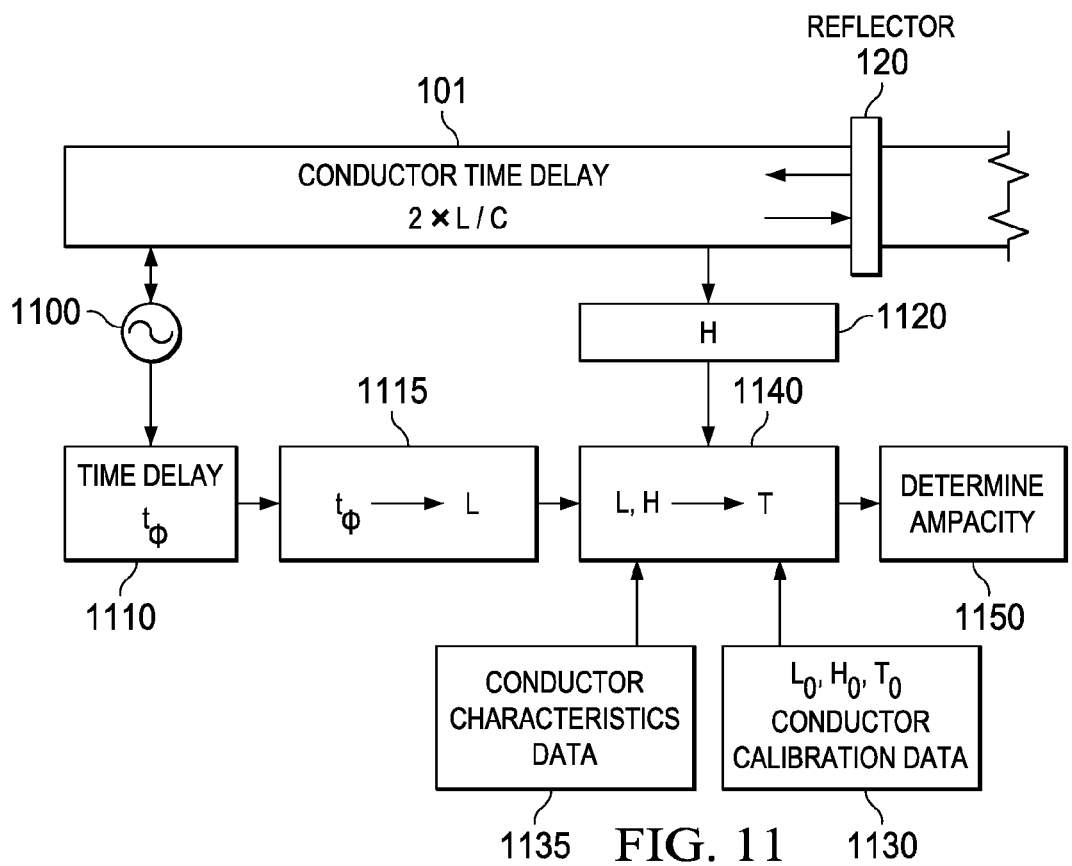
FIGS. 9 and 10 illustrate how a modified catenary equation is used to calculate average conductor temperature from conductor length and other variables.
FIG. 11 illustrates a generalized method of determining average conductor temperature of an electrical power transmission line.

FIGS. 9 and 10 illustrate how a modified catenary equation is used to calculate average conductor temperature from conductor length and other variables. FIG. 9 illustrates how length, L, may be expressed as a function of temperature, T, tension, H, and other variables. The reference values for tension and length, $H_0$ and $L_0$, are values taken at a known temperature $T_0$, and are provided by calibration process 22.

FIG. 10 illustrates how the same data can be solved for average conductor temperature. In general, this equation for temperature, T, is a combination of an equation representing the catenary shape of the conductor and an equation representing the effect of temperature on its length. The catenary equation is reflected in the term containing the hyberbolic cosecant (csch) function.

The following list explains the variables used in the catenary equations of FIGS. 9 and 10:

H Horizontal component of conductor tension measured at an attachment point $H_0$ Horizontal tension measured at a prescribed point in time, $T_0$, and used as a reference value w Conductor weight per unit length l Span length in feet measured as a straight horizontal line connecting two adjoining tower conductor attachment points L Length of the conductor suspended between two adjoining tower attachment points $L_0$ The length of the conductor measured at a prescribed point in time and used as a reference value T The average conductor temperature of the conductor within the measured length $T_0$ The average conductor temperature of the conductor measured at a prescribed point in time, $T_0$, and used as a reference value $E_0$ Modulus of elasticity for the conductor A Conductor cross-sectional area $\alpha T$ Coefficient of thermal expansion $\in_C$ Plastic deformation of the conductor due to inelastic deformation and creep.

As can be seen from FIG. 10, the average conductor temperature is calculated based on a number of variables. In particular, T is a function of the measured length and tension. It is further a function of calibrated (reference) values of length, tension, and temperature. In general, the equation of FIG. 10 solves for the average conductor temperature, T, with a geometric expression for a catenary that is modified to mathematically express the thermal elongation of an elastic, suspended, current-carrying transmission line.

Referring again to FIG. 1, the average conductor process 28 provides a new average conductor temperature for every new value of length and tension.

The average conductor temperature values are in turn delivered to controller 100, which can now use each new temperature value to more accurately determine how much current the conductor 101 is capable of carrying for that associated temperature. The actual capacity may then be used to determine the actual distribution of power that the conductor may safely carry. The distribution of power is thereby based on, largely or in part, the average temperature data.

The system of FIG. 1 may be enhanced to provide a method of detecting faults on the transmission line. Referring again to FIG. 4, for this application, distance estimate process 29 computes incidental high-impedance reflection point coordinates. The reflection localization method localizes the reflections by producing the reflection point coordinates. The method uses the conductor length estimates along with GIS and as-built information provided by the invention operator to translate conductor length into the coordinates of a given reflection point.

FIG. 11 illustrates a generalized method of determining average conductor temperature of an electrical power transmission line, consistent with the above description, to further determine its present ampacity. The method estimates the average conductor temperature T by measuring the conductor length L and the horizontal conductor tension component H.

In Step 1100, the method transmits a known waveform along the conductor 101 to a reflection point 120 at another point on the conductor. The reflection point 120 sends the waveform back to its source.

In Step 1110, the phase difference between the applied waveform and the received waveform is measured. The phase difference is converted into a time delay. Various methods may be used for obtaining an accurate measure of the delay time between the applied and reflected signals.

In Step 1115, the delay time is used to calculate the present length of the conductor.

Step 1120 is measuring the tension of the conductor. A strain gauge may be used to measure tension.

Step 1130 is providing reference values for tension $H_0$ and length $L_0$, taken at a known temperature $T_0$.

Step 1135 is providing various values for characteristics of the conductor, as described above.

In Step 1140, the reference values, measured values and conductor characteristic values are applied to a modified catenary equation to arrive at a present value for the average conductor temperature T.

Step 1150 is using the average conductor temperature to determine how much current the conductor can safely carry.

What is claimed is:

1. A method of controlling the amount of electrical power delivered to an electric transmission line (conductor), comprising:
    applying an electrical signal to the conductor;
    detecting a reflection signal reflected from a reflection point on the conductor;
    using processing equipment to perform the following: calculate the reflection propagation delay of the reflected signal; calculate the present length of the conductor based on the propagation delay; receive data representing the present tension of the conductor; receive data representing conductor reference parameters, comprising a reference tension value and reference length value both taken at a reference temperature value; receive data representing conductor characteristic parameters, comprising conductor weight, span length, elasticity, thermal expansion, and plastic deformation; and calculate the average temperature of the conductor based on the present length, present temperature, reference parameters and characteristic parameters;
    delivering average temperature data to a transmission capacity controller; and
    dispatching power to the conductor based on the average conductor temperature data.

2. The method of claim 1, wherein the reflection signal is an electrical signal reflector permanently placed on the transmission line.

3. The method of claim 1, further comprising placing an electrical signal reflector on the conductor to provide a reflection point.

4. The method of claim 1, further comprising storing data representing locations on the conductor that reflect all or part of the applied signal other than the reflection point and differentiating among reflections within the reflection signal.

5. A system for controlling the amount of electrical power delivered to an electric transmission line (conductor), comprising:
    a signal generator/detector operable to apply an electrical signal to the conductor and to detect a reflection signal reflected from a reflection point on the conductor;
    a length/temperature processor operable to perform the following: calculate the reflection propagation delay of the reflected signal; calculate the present length of the conductor based on the propagation delay; receive data representing the present tension of the conductor; receive data representing conductor reference parameters, comprising a reference tension value and reference length value both taken at a reference temperature value; receive data representing conductor characteristic parameters, comprising conductor weight, span length, elasticity, thermal expansion, and plastic deformation; and calculate the average temperature of the conductor based on the present length, present temperature, reference parameters and characteristic parameters; and
    a transmission capacity controller operable to received average temperature data from the length/temperature processor and to dispatch an amount of electrical power to the conductor based on the average conductor temperature data.

6. The system of claim 1, wherein the reflection signal is an electrical signal reflector permanently placed on the transmission line.

7. The system of claim 5, further comprising a fault differentiation processor operable to store data representing signals reflected from faults within the transmission line and to differentiate the signal reflected from the reflection point from signals reflected from faults.

* * * * *